(12) United States Patent  
Perez

(10) Patent No.: US 7,762,993 B2
(45) Date of Patent: Jul. 27, 2010

(54) CATHETER SYRINGE CONVEYOR WITH A NEEDLE GUARD HOUSING

(76) Inventor: James Gerard Perez, 4084 Bonita Rd., Bonita, CA (US) 91902

( * ) Notice: Subject to any disclaimer, the term of this patent is extended or adjusted under 35 U.S.C. 154(b) by 669 days.

(21) Appl. No.: 11/557,496

(22) Filed: Nov. 8, 2006

(65) Prior Publication Data

US 2007/0244438 A1 Oct. 18, 2007

Related U.S. Application Data

(60) Provisional application No. 60/788,747, filed on Mar. 30, 2006.

(51) Int. Cl.
*A61M 5/32* (2006.01)
(52) U.S. Cl. .................. 604/197; 604/116; 604/165.01; 604/178; 604/180; 604/181; 604/182; 604/183; 604/184; 604/187; 604/227; 604/268
(58) Field of Classification Search ................. 604/116, 604/165.01, 178, 180–184, 187, 197, 198, 604/227, 268
See application file for complete search history.

(56) References Cited

U.S. PATENT DOCUMENTS

| | | | | |
|---|---|---|---|---|
| 4,170,993 A | * | 10/1979 | Alvarez | 604/180 |
| 4,425,120 A | * | 1/1984 | Sampson et al. | 604/198 |
| 4,966,589 A | * | 10/1990 | Kaufman | 604/174 |
| 4,988,339 A | * | 1/1991 | Vadher | 604/197 |
| 4,994,045 A | * | 2/1991 | Ranford | 604/198 |
| 5,024,660 A | * | 6/1991 | McNaughton | 604/110 |
| 5,102,394 A | * | 4/1992 | Lasaitis et al. | 604/164.08 |
| 5,176,650 A | * | 1/1993 | Haining | 604/164.08 |
| 5,186,712 A | * | 2/1993 | Kelso et al. | 604/165.03 |
| 5,312,359 A | * | 5/1994 | Wallace | 604/164.08 |
| 5,320,608 A | * | 6/1994 | Gerrone | 604/117 |
| 5,462,533 A | * | 10/1995 | Daugherty | 604/164.01 |
| 5,527,290 A | * | 6/1996 | Zadini et al. | 604/165.02 |
| 5,645,076 A | * | 7/1997 | Yoon | 604/165.01 |
| 5,879,338 A | * | 3/1999 | Mahurkar | 604/195 |
| 5,893,845 A | * | 4/1999 | Newby et al. | 604/198 |
| 5,911,707 A | * | 6/1999 | Wolvek et al. | 604/116 |
| 5,951,523 A | * | 9/1999 | Osterlind et al. | 604/192 |
| 6,102,920 A | * | 8/2000 | Sullivan et al. | 606/147 |
| 6,258,064 B1 | * | 7/2001 | Smith et al. | 604/164.12 |
| 6,325,781 B1 | * | 12/2001 | Takagi et al. | 604/198 |
| 6,547,762 B1 | * | 4/2003 | Botich et al. | 604/110 |
| 6,958,054 B2 | * | 10/2005 | Fitzgerald | 604/162 |
| 7,052,483 B2 | * | 5/2006 | Wojcik | 604/162 |
| 7,314,462 B2 | * | 1/2008 | O'Reagan et al. | 604/164.08 |
| 7,318,816 B2 | * | 1/2008 | Bobroff et al. | 604/136 |
| 7,422,572 B2 | * | 9/2008 | Popov et al. | 604/198 |
| 7,473,222 B2 | * | 1/2009 | Dewey et al. | 600/210 |
| 7,578,805 B2 | * | 8/2009 | Hwang | 604/192 |
| 2005/0148945 A1 | * | 7/2005 | Chen | 604/198 |

* cited by examiner

*Primary Examiner*—Nicholas D Lucchesi
*Assistant Examiner*—Scott Medway

(57) ABSTRACT

A catheter syringe conveyor with a needle guard housing is adapted to facilitate the insertion of a catheter into a targeted blood vessel. A catheter syringe is slidably situated within a hand-held housing structure; a syringe holder that is slidably connected to the housing allows a technician to maneuver the catheter syringe up and down within the housing. At least one stabilizer finger is attached to the bottom of the housing. After a blood vessel is penetrated by the needle of the catheter syringe, the technician maneuvers a catheter pusher to lower the catheter off of the needle and into the blood vessel. After the catheter is inserted, the technician is able to slide the catheter syringe back up within the housing to move the needle within the protective walls of the housing for safety, and a syringe lock holds it there securely for safekeeping.

23 Claims, 10 Drawing Sheets

CATHETER SYRINGE CONVEYOR WITH A NEEDLE GUARD HOUSING

This application claims the benefit of U.S. Provisional Application No. 60/788,747 filed on Mar. 30, 2006.

BACKGROUND OF THE INVENTION

1. Field of Invention

This invention relates generally to catheter insertion devices, specifically to a catheter syringe conveyor with a needle guard housing.

2. History of Technology

In order to install an indwelling catheter into a blood vessel of a patient, a medical technician will often struggle with the fact that the targeted blood vessel may tend to move away from an incoming introducer needle. A second problem is that the needle is exposed for a substantial length of time during the procedure, limiting safety. A third problem arises when the targeted blood vessel is an artery; the artery is often difficult to locate. A fourth problem is that it is difficult for the technician to maintain a straight path of insertion. A fifth problem is that it is typically impossible to keep exposed fingers away from the puncture site. The present invention solves these problems.

An indwelling venous catheter is inserted into a targeted blood vessel of a patient by a qualified technician, typically for the purpose of infusing liquid substances into the patient or for occasionally removing venous blood from the patient. The catheter is inserted using a catheter syringe. After the catheter is inserted properly, the syringe is removed, and the catheter is secured to the patient.

Although the present invention is adapted for use with both venous and arterial catheters, for the purpose of clarity, this discussion will focus mostly on arterial catheters, also known as arterial lines, a-lines, or art lines. An arterial catheter is inserted into a selected artery of a patient by a technician, usually in a critical care environment within a healthcare facility. Arterial catheters are used typically for blood pressure monitoring and for patients who are in need of frequent arterial blood draws. A variety of catheters are available; a standard 20-gauge straight intravenous catheter is one type that is frequently used. The radial artery is the insertion site of choice, but other arterial sites may be used if necessary; these alternative sites include the femoral, brachial, ulnar, axillary, and dorsalis pedis arteries. Arterial blood sampling is achieved utilizing a separate access port placed onto the catheter hub of the inserted catheter, and may be performed for blood collection and for blood gas analysis. Arterial blood gas analysis is performed to determine at least the partial pressures of oxygen (PaO2) and carbon dioxide (PaCO2), and the pH of the blood sample. These values are important in assessing pulmonary function, since these measurements indicate the status of gas exchange between the lungs and the blood.

The catheter is retained over the introducer needle of a catheter syringe. When the technician inserts the introducer needle into the artery, a flash of blood in the blood receptacle of the syringe signals the technician that proper placement of the needle within the artery has occurred. The catheter is then slid off of the introducer needle by hand, deeper into the artery, and the needle is removed from within the catheter, leaving only the catheter in the artery. The catheter hub is then connected to a transducer tubing system, and then the catheter hub is secured to the patient's wrist.

A variation of the standard arterial catheter syringe is a syringe with a guide wire unit attached. The guide wire is used to help guide the catheter into the artery; after the technician has inserted the introducer needle properly into the artery, the technician advances the guide wire through the hollow needle and into the artery, providing a feed over which the catheter can be fed into the artery.

A modified Allen Test (collateral circulation test) should always be performed by the technician before inserting a needle and catheter into a patient's radial artery. The Allen Test determines if blood is capable of flowing through the ulnar artery. The ulnar artery is the only other source of blood to the hand aside from the radial artery. A negative test result is indicative of inadequate collateral blood supply to the hand and requires the selection of another location as the site for catheter insertion.

The catheter insertion procedure is difficult and prone to errors, even when the technician has ample experience. Because of the traumatic nature of the procedure, and the large number of complications that may arise from complications, it is important for the technician to try to insert the catheter properly on the first attempt. Prior art has seriously failed to provide technicians with adequate means to insert an arterial catheter regularly on the first attempt.

An unrestrained blood vessel may tend to move away from an incoming needle, particularly in older patients whose skin has become loose and has lost elasticity. A loss of elasticity in the skin creates a loss of stability around the blood vessel, which allows the vessel to roll around under the surface of the skin. It is possible for a needle to push the vessel away from its path, causing the technician to miss the targeted vessel completely. The present invention solves this problem by providing a blood vessel stabilizer to hold the vessel in place during a catheter insertion attempt.

Currently, the technician will press her or his finger over an anticipated arterial puncture site and then estimate where the artery lies under that finger; it is a rough estimate and the technician often miscalculates. Alternatively, the technician may place two fingers over the artery and attempt to hold the artery in place between the fingertips, inserting the needle between the two fingertips to attempt to penetrate the artery. This method has its limitations; the technician should have a tight pair of gloves, cannot have long finger nails, and will rely on bulky finger tips to pinpoint a relatively thin artery between them, and this technique is impossible to use on infants and small children. One embodiment of the present invention uses a blood vessel stabilizer to hold the artery within two integrated stabilizer fingers at the base of the device, and it partially occludes the artery during use; this creates a stable and augmented pulse at the site where the needle will enter the artery, thus simplifying palpation of the artery and vastly diminishing the labor involved in identifying where to insert the needle. A blood vessel stabilizer further allows the technician to keep any exposed extremities away from the puncture site while inserting the needle into the site, thus improving safety.

Because of low blood pressure, a patient's pulse may be weak and hard to locate. It is sometimes necessary for the technician to perform an arterial puncture "blindly," merely stabbing the site where the technician considers the best option for obtaining arterial access. The present invention helps to create an augmented pulse that is palpable even in cases of low blood pressure.

Most protocols allow a technician to try three consecutive needle insertions without removing the needle tip beyond the subcutaneous tissue. As the angle of insertion changes within the dermis, the needle slices through the tissue in its path, and may even lacerate the artery. Any change in the angle of needle insertion can inflict severe pain onto a conscious patient.

Because of the structural design of the present invention, a straight, unswerving path of needle insertion into the blood vessel is assured. Currently, the often unsteady hand of the technician is used to guide the needle down into the blood vessel. A nervous hand can become quite jittery, and even a calm hand does not guarantee a straight path of insertion into and out of the vessel. The present invention provides a considerable improvement in this regard; pressing the stabilizer, at the base of the invention, down near the insertion site provides stability to the hand of the technician. The straight slot within the housing, which supports the syringe, vastly improves the likelihood of a direct and controlled line of insertion and extraction of the needle during a catheter insertion procedure, minimizing pain and trauma within the patient's dermal tissues and artery.

Often, the unrestrained nature of the current methods for inserting a catheter into a blood vessel causes the introducer needle to become accidentally extracted from within the blood vessel during a catheter insertion attempt. The present invention prevents this common mishap, by providing a solid, steady housing within which the syringe is securely held in place during the procedure.

According to standard procedure protocols, a catheter introducer needle should enter an artery at a steady angle of 30 to 45 degrees in relation to the artery; prior art relies on the technician to maintain that angle without any support. A proper angle of needle insertion is assured using one embodiment of the present invention, as a result of the base of the stabilizer fingers being angled in relation to the housing slot within which the syringe is maneuvered.

PRIOR ART

Prior art includes devices that help a technician insert a catheter into a blood vessel, and also devices that stabilize a blood vessel during the insertion of a needle therein.

Most of the devices within the realm of prior art do not address the issue of safety adequately. Most catheter insertion devices require the integrated needle to be exposed during much of the procedure; this can be hazardous to technicians and patients if the syringes are handled improperly or unsteadily, as may commonly occur in emergency situations. Needle sticks are the most frequent source of transmission of blood borne disease in healthcare workers. In most of the devices of prior art, the needle is exposed before and after the insertion procedure and there are no means provided to protect personnel from contact with the needle during the procedure. Some devices have disclosed means to withdraw the introducer needle into a safety enclosure after successful insertion of the catheter, but they do not go far enough to prevent injuries and they are difficult to use. Using the current invention, the needle is exposed for only a short period during the entire procedure; the needle is lowered and exposed only after the device has been set over the targeted insertion site. Immediately after the catheter is inserted into the blood vessel, the needle is safely withdrawn out of the blood vessel and back into the protective walls of the housing only one hand.

Another limitation of prior art is that stability of the device during the procedure is lacking. The stabilizer of the present invention is pressed down near the insertion site to provide stability to the hand of the technician, and a straight path of needle insertion is assured, limiting tissue damage.

Several devices have been proposed for stabilizing a vein for venipuncture, but none of the devices provide proper support for arterial puncture. For arterial puncture, the blood vessel stabilizer portion of the device should be relatively small to accommodate the limited space over the radial artery near the hand, and it should be shaped to facilitate palpation of the targeted puncture site by the technician. The device should be designed to allow a proper angle of needle passage into the artery, and it should be easily removed from the puncture site; it cannot be bound or taped down during use. These beneficial features are all present in the current invention.

The present invention may be used on any artery, not just the radial artery. The present invention includes a syringe holder slidably maneuvered within a housing frame to help guide the introducer needle steadily into and out of the artery. The present invention allows the technician to release the pressure over the artery before removing the needle from the insertion site.

The present invention can be adapted to integrate any one of a large variety of catheter syringes. The present invention may further include an adjustable stabilizer to accommodate targeted blood vessels of various sizes.

OBJECTS AND ADVANTAGES

Accordingly, several objects and advantages of the present invention include providing a catheter syringe conveyor that:

(a) slidably retains a catheter syringe and renders a straight path of needle passage into and out of the blood vessel.

(b) allows the introducer needle to be immobilized safely within the housing.

(c) is held in place using only one of the technician's hands.

(d) helps the technician to keep the tip of the needle steadily within the blood vessel.

(e) shields the technician's fingers from the sharp needle tip during use, to prevent injury.

(f) can be used on any individual of any age and size, and on any suitable blood vessel.

(g) can integrate a large variety of catheter syringes, including one with a guide wire.

(h) minimizes the need for multiple attempts to penetrate the blood vessel.

(i) assures a proper angle of needle insertion into a blood vessel.

(j) allows unrestricted blood flow through the ulnar artery when the radial artery is targeted.

(k) holds a blood vessel in place during the insertion of a catheter into the vessel.

(l) isolates an artery and creates an augmented pulse for easy identification of the location of the artery.

(m) is inexpensive to manufacture, simple and intuitive to use, disposable, and light-weight.

(n) allows the technician to regulate the pressure of the device above a blood vessel.

(o) allows the technician to alter the width between each stabilizer finger.

DETAILED DESCRIPTION OF THE INVENTION

Figure 1A:
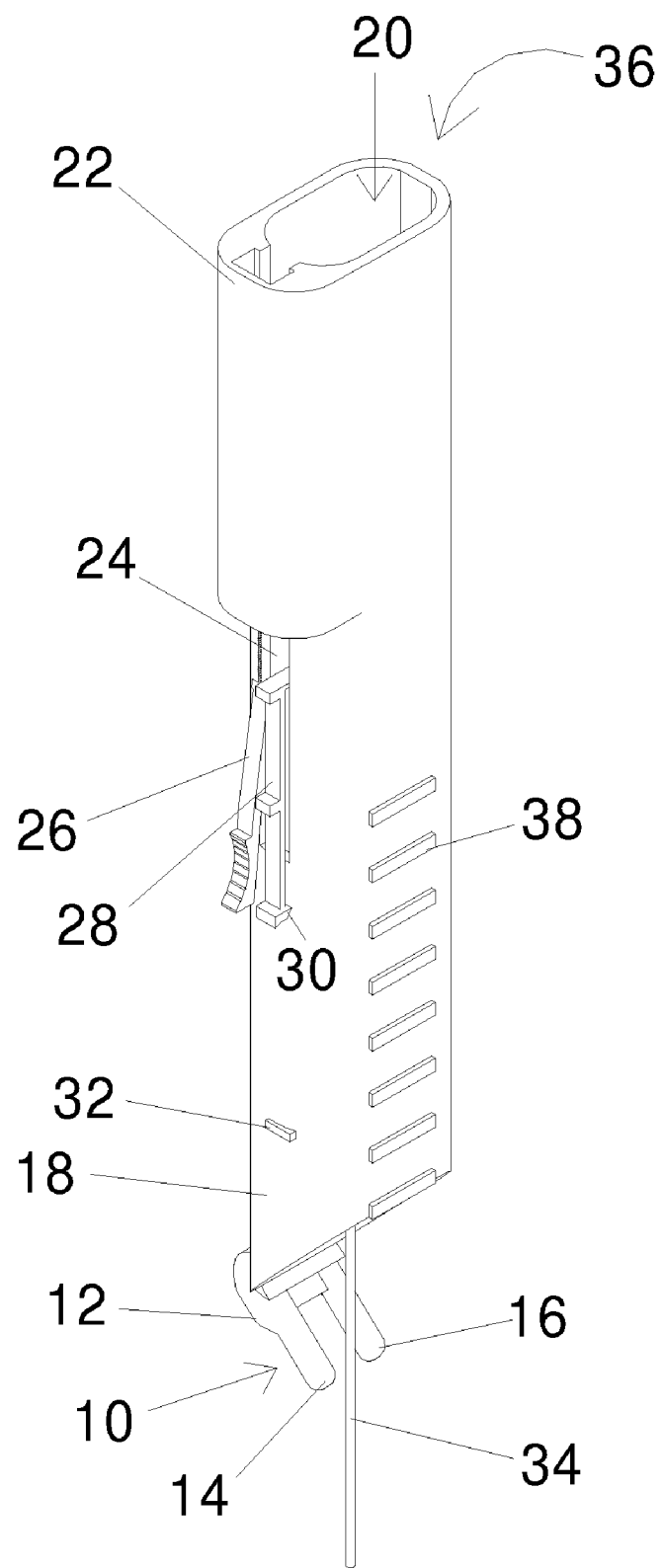
FIG. 1A is an upper left perspective view of one embodiment of the invention having a stabilizer specifically designed for use with arterial punctures, depicting aspects of the invention including a housing, a stabilizer attached at the bottom end of the housing, a catheter protruding from an access aperture at the bottom end of the housing, and a syringe holder arm and catheter pusher arm emanating from a housing slit.

Referring now to the drawings, FIGS. 1A-6 represent various embodiments and designs of the present invention. Each embodiment has the novelty of employing a syringe holder and a catheter pusher slidably positioned relative to a protective housing, a housing slit through which the syringe holder is activated, and a stabilizer that is pressed against the patient to stabilize the device during use. Turning first to FIG. 1A, stabilizer 10 includes base 12 and stabilizer fingers 14 and 16. Stabilizer fingers 14 and 16 emanate from base 12. A targeted artery is positioned by the technician between stabilizer fingers 14 and 16. Alternatively, only one finger protrudes from base 12; the single finger would hold only one side rather than both sides of a targeted artery. A single stabilizer finger could be pressed against one side of a radial artery while the patient's tendons press up against the opposite side of the artery to hold the artery in place. Housing 18 is attached to base 12. Stabilizer fingers 14 and 16 serve to stabilize housing 18 as well as to stabilize a targeted artery during use. The bottom surface of each stabilizer finger is angled relative to housing 18. The angle may be 30 degrees, 45 degrees, any angle between 30 and 45 degrees, or any other angle suitable for the procedure. Housing slot 20 runs through housing 18. A catheter syringe is situated within housing slot 20 and is lowered within housing slot 20 by the technician to guide the needle of the syringe down into the targeted artery; the needle passes between and beyond the tips of stabilizer fingers 14 and 16 as shown. Housing bridge 22 connects each side of housing slit 24. Syringe holder arm 26 and catheter pusher arm 28 emanate through housing slit 24 from inside of housing slot 20 for access by the technician. Housing slot 20 channels the syringe holder (not shown) along a straight pathway so that the needle enters and exits a targeted artery along a consistent axis. Catheter pusher arm tooth 30 is capable of locking over catheter pusher arm stop 32 when catheter pusher arm 28 has been slid down housing 18 far enough by the technician; this locks catheter pusher arm 28 in place, facilitating access to the catheter hub of catheter 34 by the technician. The syringe and the catheter pusher, with everything attached thereon, are inserted through top end 36 of housing 18 during assembly of the device, preferably accomplished by the manufacturer prior to distribution. Housing ridges 38 help the technician securely grip housing 18 during use.

Figure 1B:
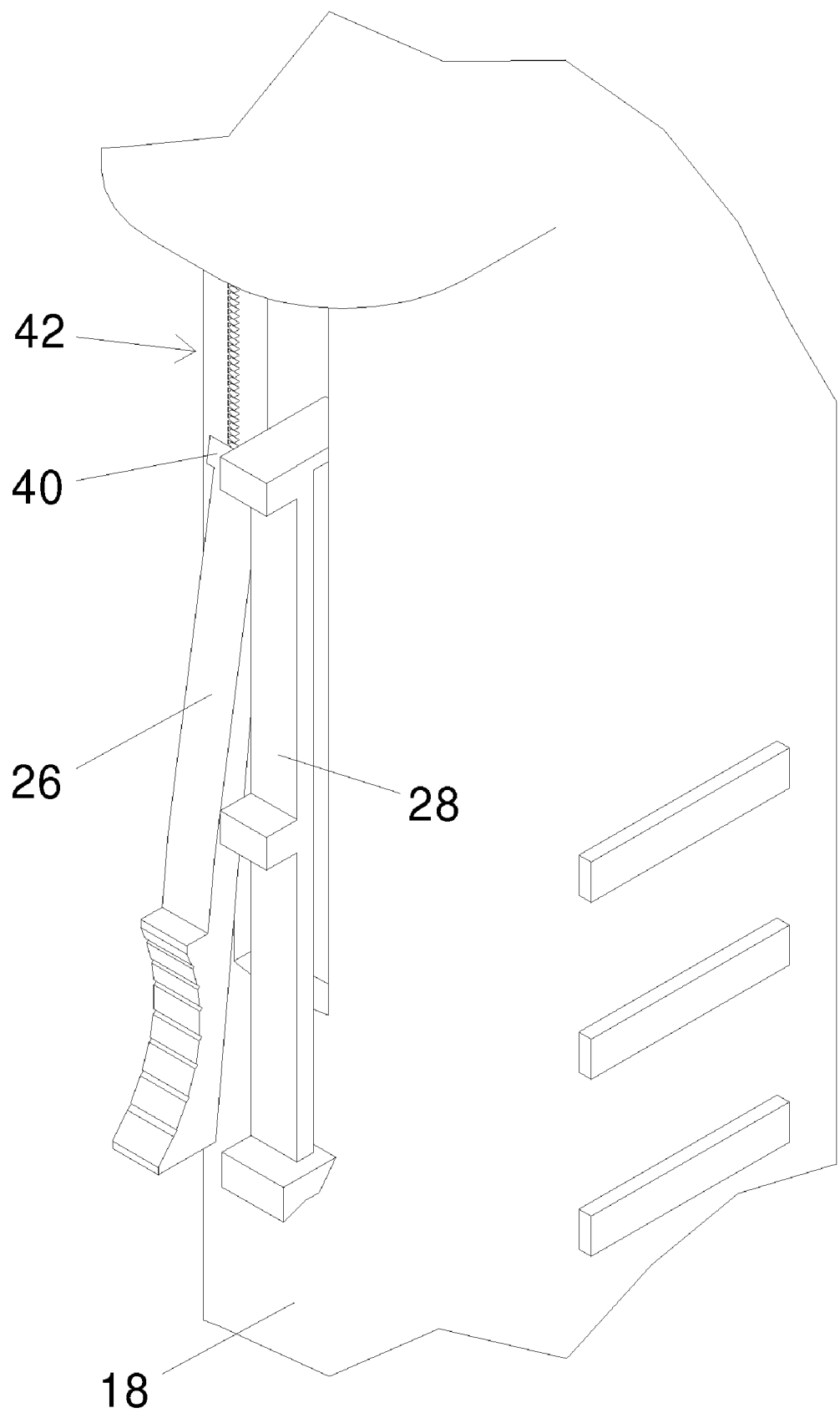
FIG. 1B is an enlarged partial perspective view of the device in FIG. 1A, focusing on the syringe holder arm, the catheter pusher arm, and a series of notches within which a locking tooth may be locked.

Turning to FIG. 1B, syringe holder arm locking tooth 40 engages within one notch of the series of notches 42 cut along a linear path within housing 18; this acts as a syringe lock because syringe holder arm 26 is locked in place, and syringe holder arm 26 is connected to the syringe holder (not shown). The notch receives the locking tooth thereby acting as a syringe lock receiver.

Figure 1C:
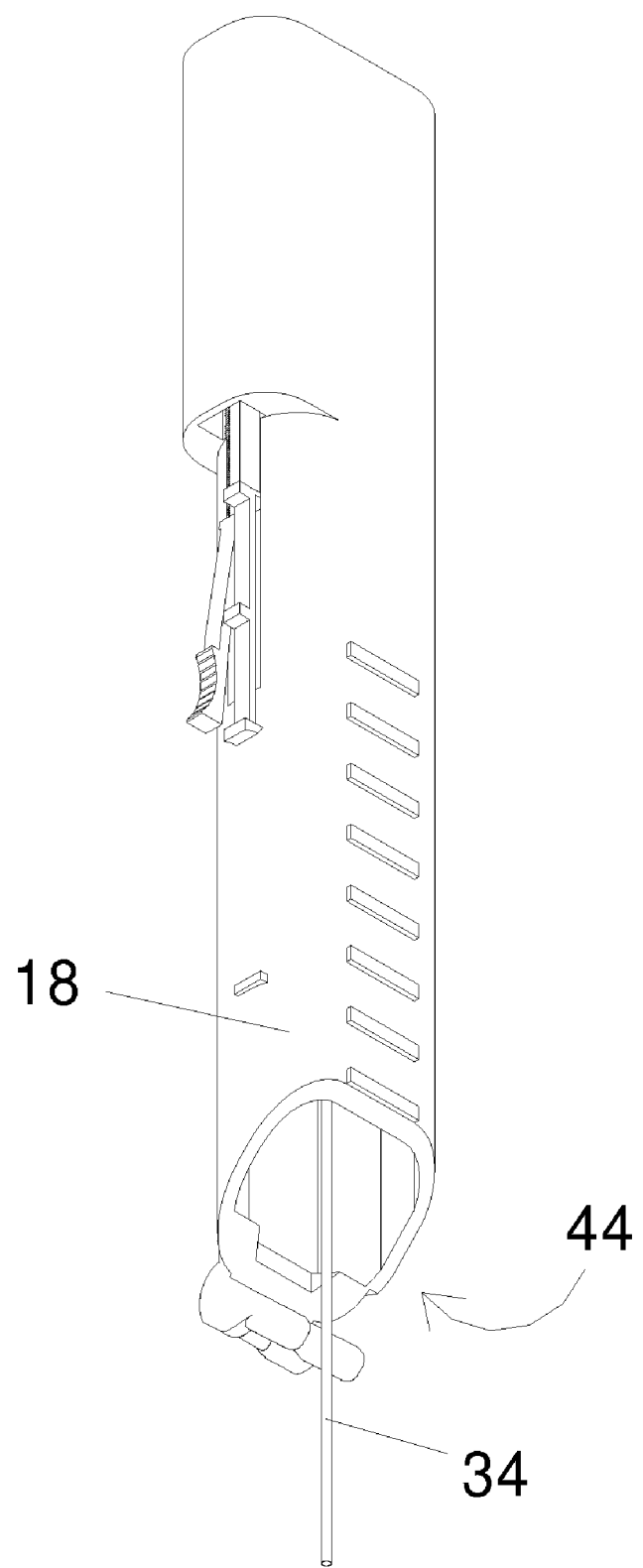
FIG. 1C shows a lower left perspective view of the access aperture at the bottom end of the housing.

Looking at FIG. 1C now, access aperture 44 at the bottom end of housing 18 provides ample space through which the technician may grasp the catheter hub of catheter 34 when it is time to do so during the procedure.

Figure 1D:
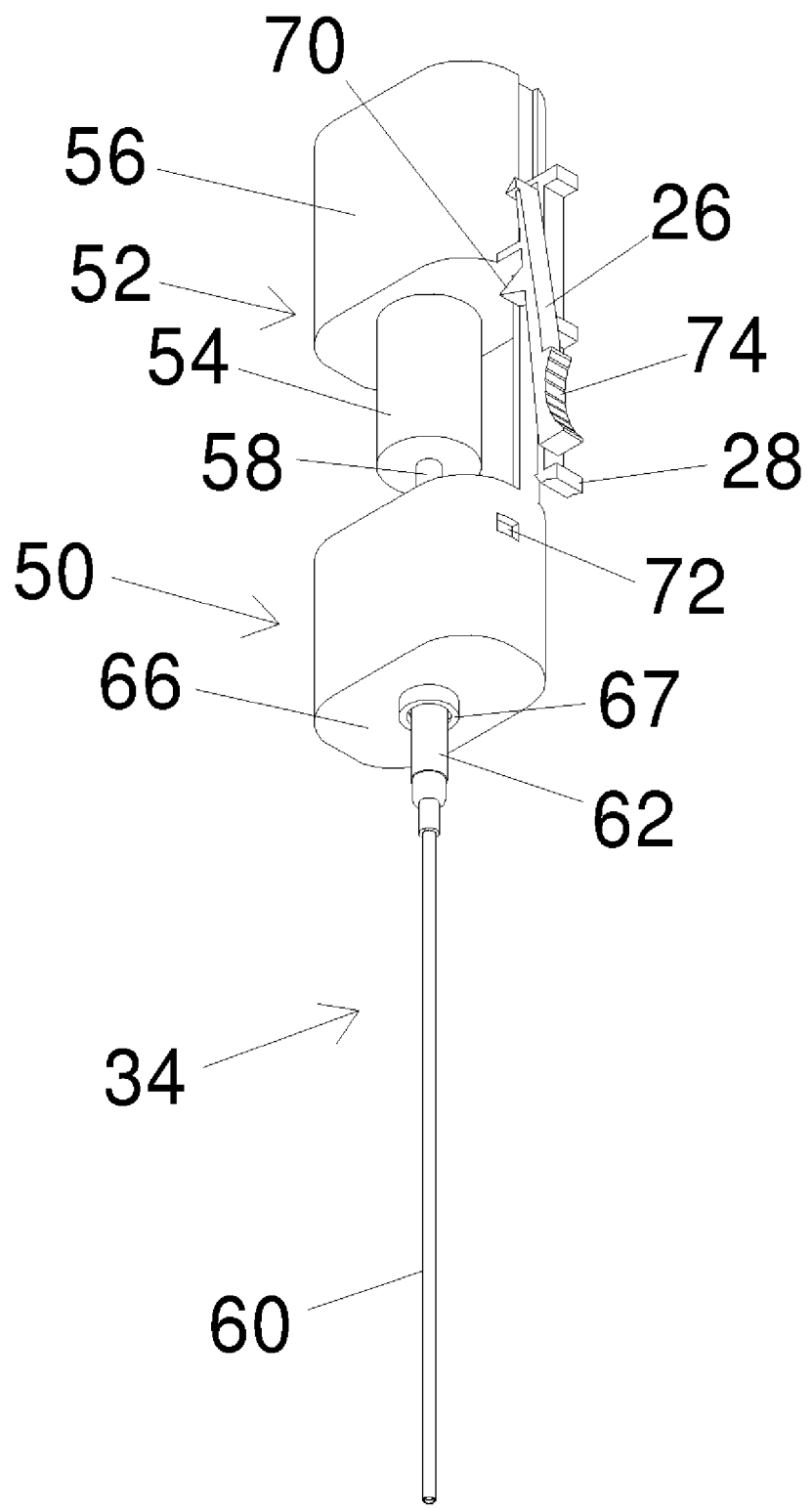
FIG. 1D shows a lower perspective view of the syringe holder and the catheter pusher as they would be positioned within the housing in FIGS. 1A-1C, with the housing removed. The catheter pusher is shown separated from the syringe holder for illustrative purposes.

Turning next to FIG. 1D, catheter pusher 50 is disposed below syringe holder 52 within the housing slot (not shown). Blood receptacle 54 is slidably retained within the housing slot by syringe holder body 56. Alternatively, syringe holder arm 26 may be connected directly to blood receptacle 54; in this case, it would be necessary to configure blood receptacle 54 with a certain shape that matches the shape of the housing slot through which it is slid, and the exterior wall of the blood receptacle acts as the syringe holder. Needle 58 is attached to blood receptacle 54. Needle 58 passes through catheter pusher 50. Catheter 34 is removably positioned over needle 58. Catheter pusher 50 is shown slightly separated from syringe holder 52 for illustrative purposes. As positioned, the tip of needle 58 would reside at location 60 within catheter 34. During a catheter insertion procedure, catheter pusher 50 would continue to be maneuvered by the technician down the housing slot until it reached the bottom of the housing. At that juncture, the technician would raise needle 58 out of the artery and back into the protective walls of the housing. Catheter hub 62 would be grasped by the technician, released from catheter hub connector 67, and held in place over the artery as the rest of the device is removed and set aside or discarded safely. Catheter hub connector 67 can have a threaded surface (not shown) to retain catheter hub 62; in order to remove catheter hub 62 from catheter hub connector 67, the technician would twist catheter hub 62 off of the threaded catheter hub connector. In the displayed embodiment, catheter hub connector 67 is attached to push member 66. Alternatively, a catheter hub connector is not included, and instead, catheter hub 62 merely resides over needle 58 directly adjacent push member 66; in this scenario, push member 66 would push catheter hub 62 down over needle 58 as catheter pusher 50 is maneuvered by the technician down the housing. In another alternative embodiment, blood receptacle 54 would have a protuberance at the point where needle 58 is attached to it, and the protuberance would act as a catheter hub connector, and push member 66 would be positioned between blood receptacle 54 and catheter hub 62; push member 66 would serve to push catheter hub 62 off of the protuberance and then down the needle during a catheter insertion procedure. Syringe holder arm engagement tooth 70 enters within catheter pusher engagement seat 72 when each is properly aligned and syringe holder arm 28 is maneuvered appropriately by the technician; the technician presses down on syringe holder arm finger contact 74 to accomplish this. The engagement of engagement tooth 70 within engagement seat 72 serves to allow the technician to maneuver catheter pusher 50 together with syringe holder 52 as the technician attempts to position the tip of needle 58 within the targeted artery. After the needle tip has penetrated the targeted artery, finger contact 74 is released, thus freeing engagement tooth 70 from engagement seat 72. Then, catheter pusher arm 28 is maneuvered separately by the technician, maneuvered down the housing to guide catheter 34 into the artery. Alternatively, the technician's finger could simply contact both syringe holder arm finger contact 74 and catheter pusher arm 28 simultaneously as the both are maneuvered together by the technician, without the need for an engagement tooth and a corresponding engagement seat. The technician would release finger contact 74 after the artery is penetrated, and proceed to maneuver only catheter pusher arm 28 down the housing. Another alternative is for the catheter pusher arm to be adapted to protrude out of the top opening of the housing, so that only the syringe holder arm protrudes through the housing slit; the technician would maneuver the catheter pusher arm from the top of the housing, momentarily requiring the use of the technician's free hand.

Figure 1E:
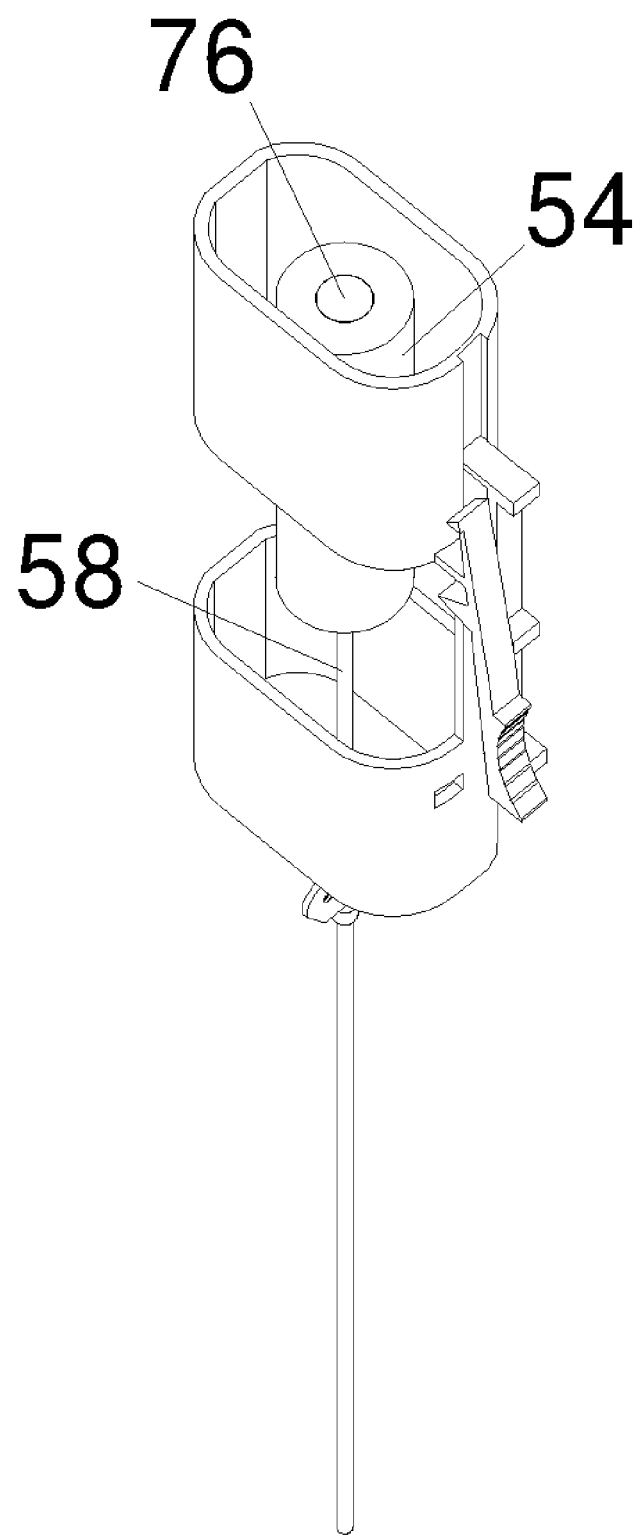
FIG. 1E shows an upper perspective view of the arrangement in FIG. 1D

Looking now at FIG. 1E, air vent 76 is located within the top end of blood receptacle 54. Needle 58 is shown more clearly here emanating from its attachment to blood receptacle 54.

Figure 2:
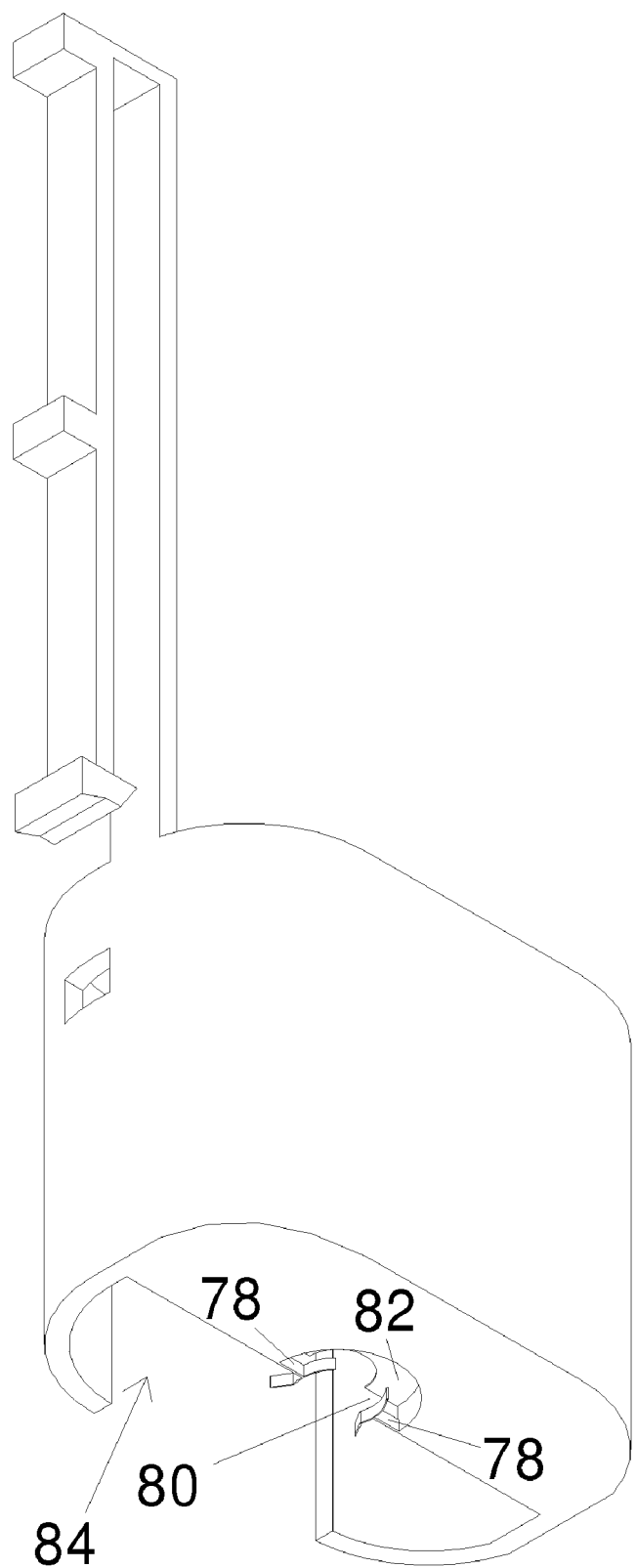
FIG. 2 is an enlarged perspective view of an alternative catheter pusher that has a special catheter hub connector with hub holder fingers that allow for easy removal of the catheter hub from the connector.

Turning now to FIG. 2, this alternative catheter pusher utilizes the special catheter hub connector illustrated. A catheter hub is placed within space 80 between hub holder fingers 78 and back wall 82. Hub holder fingers 78 are designed to allow the catheter pusher to push an attached catheter up or down over a needle. When the catheter has been inserted into the artery, the technician can remove the catheter hub from within fingers 78 by pressing the catheter hub down, in the direction of open segment 84 of the catheter pusher, so that the fingers release the catheter hub. Open segment 84 allows the catheter pusher to be installed directly over the syringe, without having to pass it over the needle first.

Figure 3:
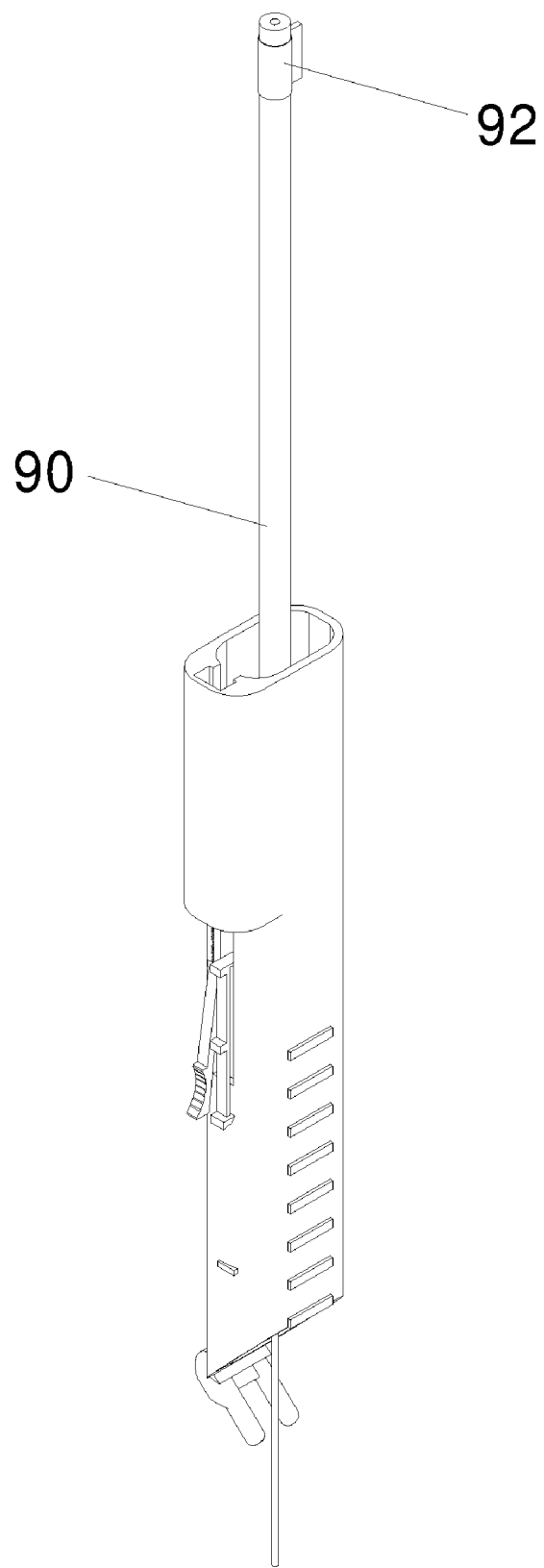
FIG. 3 is an upper left perspective view of the invention with an integrated guide wire unit.

Referring to FIG. 3, in this alternative embodiment, which utilizes a guide wire unit, guide wire enclosure 90 is attached to the top end of the syringe (not shown). A flexible guide wire is attached to guide wire handle 92 within guide wire enclosure 90. The technician maneuvers guide wire handle 92 down guide wire enclosure 90 to transmit the attached guide wire down through the blood receptacle, then further through the needle, and then into the targeted artery.

Figure 4:
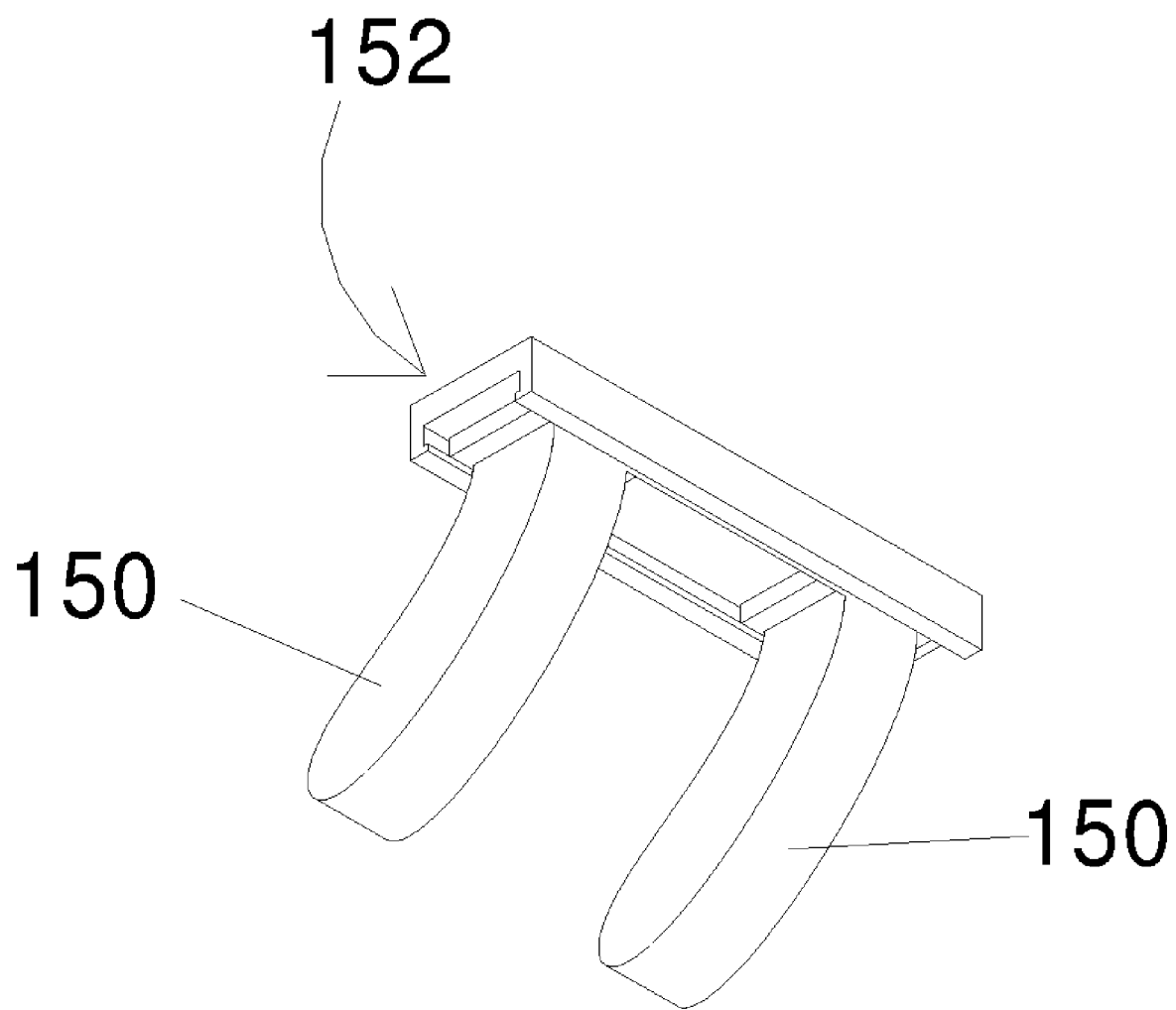
FIG. 4 is an enlarged lower rear perspective view of an alternative stabilizer with each stabilizer finger situated within an adjustment track to allow adjustability of the distance between each finger.

Turning next to FIG. 4, stabilizer fingers 150 are slidably situated within adjustment track 152 so that the distance between each finger can be altered to accommodate targeted blood vessels of various sizes. It can be designed as a more complex apparatus, such as one that requires the technician to turn a knob to alter the distance between each finger, but a simple one is shown here for ease of illustration.

Figure 5:
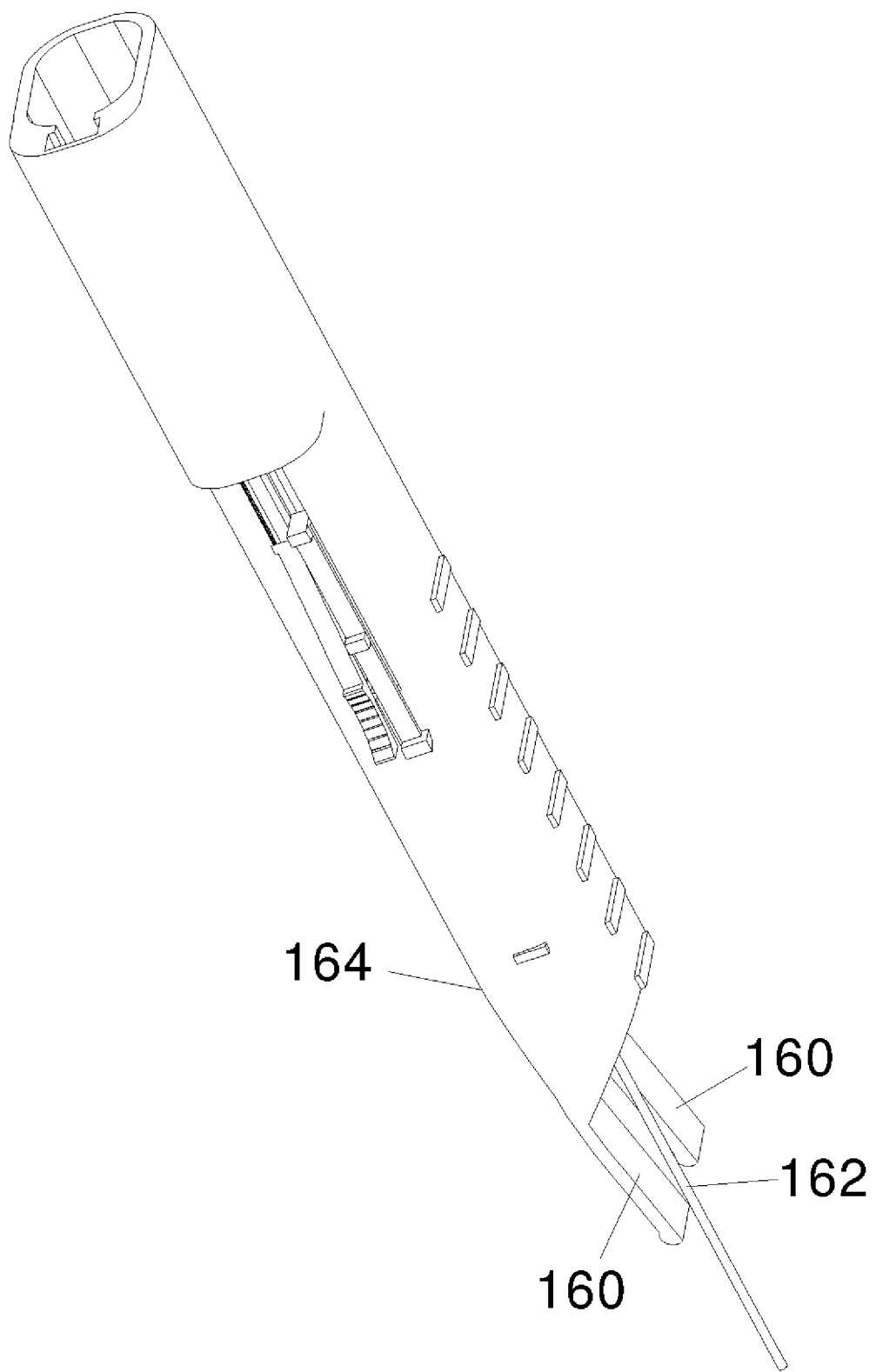
FIG. 5 is a perspective view of an embodiment, similar to the one in FIG. 1A, which has a stabilizer for use with venous catheter insertions.

Turning now to FIG. 5, stabilizer fingers 160 are adapted for venous access; a vein is situated between the stabilizer fingers during a catheter insertion attempt. The needle penetrates the vein at point 162, and the technician is able to tilt the device during the procedure. The stabilizer fingers extend at a very small angle from point 164, relative to the housing, so that after the vein has been penetrated by the needle, the housing can be brought down nearly parallel to the vein, to allow an effective angle of catheter insertion into the vein.

Figure 6:
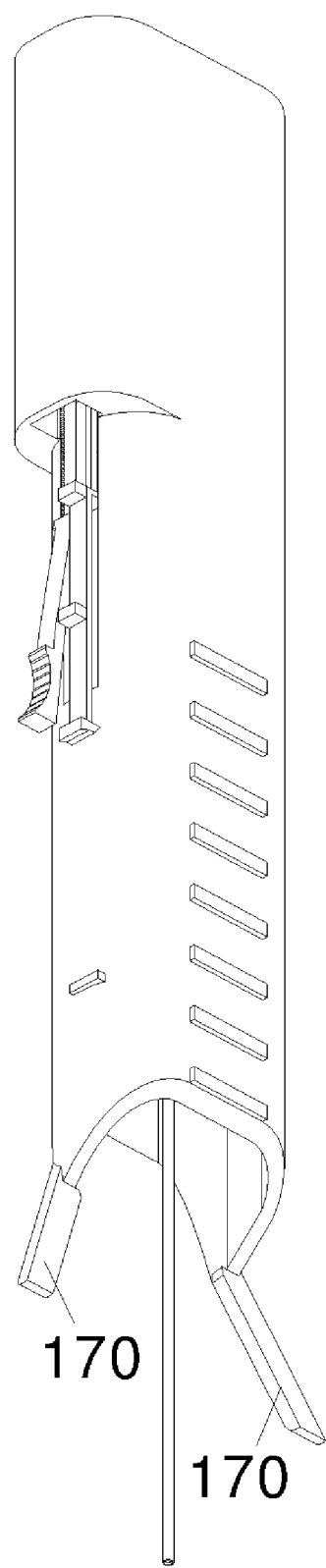
FIG. 6 is a perspective view of an embodiment having more spaced out stabilizer fingers.

Turning finally to FIG. 6, this is similar to the embodiment in FIG. 5, except stabilizer fingers 170 are spaced apart more to prevent any possible obstruction of venous blood flow through the targeted vein.

What is claimed is:

1. A catheter syringe conveyor comprising:
   a catheter syringe that comprises a needle attached to a vented blood receptacle;
   a catheter that comprises a flexible tube with a top end, a bottom end, and a catheter hub disposed at said top end of said flexible tube, wherein said catheter is removably disposed over said needle
   a housing comprising a substantially rigid and wall structure shaped to frame a housing slot through which said catheter syringe can be maneuvered, said housing being sized to be held within the grasp of a technician's hand, said housing comprising a top end, a bottom end, a longitudinal axis sited between said top end and said bottom end of said housing and a perimeter at said bottom end of said housing framing an access aperture through which said catheter hub may can be grasped by a technician during a catheter insertion procedure, wherein said perimeter at said bottom end of said housing comprises a continuous rigid wall structure that completely circumscribes said housing slot, said housing further comprising at least one housing slit cut out within a predetermined length of said housing wall structure along the same longitudinal axis as said housing, said housing slit comprising a first side and a second side lengthwise and a first end and a second end, wherein said housing slit is disposed within said housing clear of said bottom end perimeter;
   a stabilizer comprising at least one stabilizer finger with a bottom surface that contacts said skin of said patient on one side of a targeted blood vessel during said catheter insertion procedure;
   a syringe holder adapted to retain said blood receptacle component of said catheter syringe so that said catheter syringe can be maneuvered within said housing stably, said syringe holder comprising a body that is slidably connected to said housing so that said syringe holder can be maneuvered along said longitudinal axis of said housing, wherein part of said syringe holder is adapted to protrude from said housing slit for access by a technician; and
   a catheter pusher adapted to contact said catheter hub, said catheter pusher further adapted to protrude from within said housing slot and allow said technician to urge said catheter down over said needle to separate said catheter from said syringe.

2. The device of claim 1 wherein said stabilizer comprises two stabilizer fingers, each stabilizer finger comprising a bottom surface that contacts said skin of said patient on opposite sides of said targeted blood vessel during said catheter insertion procedure, and said stabilizer fingers are connected to said bottom end of said housing so that said housing positions said needle of said syringe to enter into said blood vessel between said stabilizer fingers.

3. The device of claim 2 wherein said stabilizer fingers are spaced apart so as to contact said skin above said blood vessel directly adjacent said blood vessel, to stabilize said blood vessel as well as said housing during said catheter insertion procedure.

4. The device of claim 1 further comprising a stabilizer finger adjustment track in which each stabilizer finger is set, said stabilizer finger adjustment track adapted to allow said technician to adjust the position of each stabilizer finger.

5. The device of claim 3 wherein:
   said bottom surface of each of said stabilizer fingers is elongated and positioned so that at least part of said bottom surface of each of said stabilizer fingers is angled relative to said longitudinal axis of said housing, said angle adapted to retain said syringe over an artery at a predetermined angle when said stabilizer is properly pressed onto the patient's skin above said artery, thereby providing an appropriate and steady angle of needle passage into said artery; and
   said housing positions said needle to enter said artery beyond the shortest tip of said stabilizer fingers.

6. The device of claim 1 wherein said housing comprises a first and a second housing slit, and part of said syringe holder protrudes from said first housing slit while part of said catheter pusher protrudes from said second housing slit for access by said technician.

7. The device of claim 1 wherein part of said syringe holder and part of said catheter pusher both protrude through said housing slit and are slidably situated there.

8. The device of claim 1 wherein, said syringe holder further comprises a syringe lock adapted to render said syringe immobile within said housing slot within at least one predetermined location where the tip of said needle is stationed within said housing near said bottom end of said housing.

9. The device of claim 1 further comprising a guide wire unit attached to said blood receptacle of said catheter syringe, said guide wire unit adapted to allow said technician to insert into said blood vessel a flexible feed over which said catheter can travel as said catheter is inserted into said blood vessel, wherein said housing comprises a top perimeter that frames an aperture at said top end of said housing, and said guide wire unit is adapted to emerge out from within said top perimeter at said top end of said housing.

10. The device of claim 8 wherein said syringe holder further comprises a syringe holder arm that is adapted to protrude from said housing slit for access by said technician.

11. The device of claim 10, further comprising a housing bridge that comprises a rigid structure joining at least part of each side of said housing slit, said housing bridge adapted to add structural support to said housing by closing at least part of the gap within said housing created by said housing slit, wherein said housing bridge is elevated compared to the rest of said housing to allow at least said syringe holder arm to pass within said housing bridge as said syringe holder is maneuvered within said housing.

12. The device of claim 10 wherein:
said syringe lock further comprises a locking tooth incorporated on said syringe holder arm, said locking tooth comprising a protuberance adapted to engage into a locking position along at least one section of said housing; and
said housing further comprises at least one notch cut within said housing, said notch adapted to receive and lock said locking tooth in place.

13. The device of claim 12 wherein:
said housing further comprises a series of notches cut into said housing along a linear path near said housing slit; and
said syringe holder arm further comprises a first end accessible to said technician and a second end where said locking tooth is disposed, whereby when said first end is released by said technician while said locking tooth is positioned within the boundaries of said series of notches, said locking tooth engages fixedly within one of the notches, and said locking tooth dislodges from within said notch when said technician appropriately presses on said first end, thereby freeing said syringe holder arm for movement up or down said housing, said series of notches adapted to provide multiple locations along the length of said housing to securely retain said syringe holder arm.

14. The device of claim 1 wherein said catheter pusher comprises:
a catheter pusher body shaped to slide stably up and down said housing; and
a push member attached to said catheter pusher body, said push member adapted to be situated between said blood receptacle and said catheter hub, said push member adapted to contact said catheter hub to allow said technician to push said catheter hub down over said needle.

15. The device of claim 14 wherein said catheter pusher further comprises a catheter pusher arm adapted to emanate from said catheter pusher body, said catheter pusher arm adapted to protrude out from within said housing for contact by said technician.

16. The device of claim 15 wherein:
said housing further comprises a top perimeter that is adapted to frame an aperture at said top end of said housing; and
said catheter pusher arm is adapted to emerge out of said aperture at said top end of said housing.

17. The device of claim 14 wherein said catheter pusher further comprises hub holder fingers disposed on said push member, said hub holder fingers adapted to retain said catheter hub so that said catheter hub can be pushed away from said hub holder fingers in order to release said catheter hub from said hub holder fingers.

18. The device of claim 14 wherein said push member further comprises a catheter hub connector, said catheter hub connector comprising a protuberance on which said catheter hub can be removably retained, said protuberance comprising an aperture cut out at its apex adapted to allow said needle to pass through it, said catheter hub connector adapted to allow said technician to maneuver said catheter up and down over said needle while said catheter hub remains fixed over said catheter hub connector.

19. The device of claim 15 wherein said catheter pusher arm protrudes past said housing slit for access by said technician.

20. The device of claim 1 wherein said catheter pusher and said syringe holder further comprise engaging means for allowing said technician to maneuver said syringe holder concurrently with said catheter pusher up or down said housing.

21. A catheter syringe conveyor comprising
a housing that comprises a substantially rigid and transparent wall structure shaped to frame a housing slot through which a catheter syringe may can be maneuvered, said housing being sized to be held within the grasp of a technician's hand, said housing comprising a top end, a bottom end, a longitudinal axis between said top end and said bottom end, and a perimeter at said bottom end framing an access aperture through which the hub of a catheter may can be grasped by a technician during a catheter insertion procedure, wherein said perimeter at said bottom end of said housing comprises a continuous wall structure that completely circumscribes said housing slot, said housing further comprising at least one housing slit cut out within a predetermined length of said housing wall structure along the same longitudinal axis as said housing, said housing slit comprising a first side and a second side lengthwise, said housing slit adapted to provide an opening through which at least a syringe holder can protrude from within said housing slot for access by said technician;
a stabilizer comprising at least one stabilizer finger with a bottom surface adapted to contact the skin of a patient on one side of a targeted blood vessel vessel during said catheter insertion procedure;
a syringe holder adapted to retain the blood receptacle component of said catheter syringe so that said catheter syringe can be maneuvered within said housing stably, said syringe holder comprising a body that slidably connects to said housing so that said syringe holder can be maneuvered along said longitudinal axis of said housing, wherein part of said syringe holder is adapted to protrude through said housing slit and a catheter pusher protruding from within said housing slot and allowing said technician to urge a catheter down over said needle to separate said catheter from said catheter syringe, said catheter pusher comprising a push member adapted to contact said catheter hub.

22. The device of claim 21 wherein said catheter pusher further comprises a catheter pusher arm adapted to project out from within said housing to allow said technician to maneuver said catheter pusher by maneuvering said catheter pusher arm.

23. The device of claim 21 wherein said catheter pusher further comprises a catheter pusher body with a shape adapted to allow said catheter pusher body to be slid stably up and down said housing.

* * * * *